United States Patent
Gemmel et al.

(10) Patent No.: US 10,687,900 B2
(45) Date of Patent: Jun. 23, 2020

(54) METHOD OF IMAGE SUPPORT FOR A PERSON CARRYING OUT A MINIMALLY INVASIVE PROCEDURE WITH AN INSTRUMENT IN A PROCEDURE SITE OF A PATIENT, X-RAY APPARATUS, COMPUTER PROGRAM AND ELECTRONICALLY READABLE DATA CARRIER

(71) Applicant: SIEMENS HEALTHCARE GMBH, Erlangen (DE)

(72) Inventors: Alexander Gemmel, Erlangen (DE); Bjoern Kreher, Braeuningshof (DE); Gerhard Kleinszig, Forchheim (DE); Markus Weiten, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 170 days.

(21) Appl. No.: 15/907,507

(22) Filed: Feb. 28, 2018

(65) Prior Publication Data
US 2018/0250076 A1    Sep. 6, 2018

(30) Foreign Application Priority Data

Mar. 2, 2017   (DE) .......................... 10 2017 203 438

(51) Int. Cl.
*G06K 9/00*    (2006.01)
*A61B 34/10*   (2016.01)
(Continued)

(52) U.S. Cl.
CPC .............. *A61B 34/10* (2016.02); *A61B 6/12* (2013.01); *A61B 6/5205* (2013.01);
(Continued)

(58) Field of Classification Search
None
See application file for complete search history.

(56) References Cited

U.S. PATENT DOCUMENTS

| 8,532,258 B2 | 9/2013 | Bulitta et al. |
| 2003/0088179 A1* | 5/2003 | Seeley .................... A61B 6/12 |
| | | 600/424 |

(Continued)

FOREIGN PATENT DOCUMENTS

| DE | 102009037251 A1 | 2/2011 |
| DE | 102009049818 A1 | 4/2011 |

(Continued)

OTHER PUBLICATIONS

Zhang Hua et al: "Iterative Reconstruction for X-Ray Computed Tomography Using Prior-Image Induced Nonlocal Regularization",IEEE Transactions on Biomedical Engineering, IEEE Service Center, Piscataway, NJ, USA, vol. 61, No. 9, Sep. 2, 2014 (Sep. 2, 2014), pp. 2367-2378, XP011556624, ISSN: 0018-9294.

*Primary Examiner* — Hadi Akhavannik
(74) *Attorney, Agent, or Firm* — Laurence Greenberg; Werner Stemer; Ralph Locher (57) ABSTRACT

In a method of image support for a person carrying out a minimally invasive procedure with an instrument in a procedure site of a patient, one two-dimensional X-ray image respectively of the procedure site is recorded by an X-ray apparatus in at least two recording geometries implementing different projection directions and chosen specific to the procedure, in particular by the person. A three-dimensional model data set of the procedure region is reconstructed by iterative reconstruction from the X-ray images. At least one two-dimensional supporting image corresponding to one of the recording geometries is determined by incorporating at least one item of further information by re-projection of the model data set supplemented by the further information and is displayed for the user.

16 Claims, 4 Drawing Sheets

(51) Int. Cl.
   *G06T 11/00*      (2006.01)
   *A61B 6/00*       (2006.01)
   *A61B 6/12*       (2006.01)
   *G16H 30/40*      (2018.01)
   *G06T 19/00*      (2011.01)

(52) U.S. Cl.
   CPC .......... *G06T 11/006* (2013.01); *G06T 11/008* (2013.01); *G06T 19/00* (2013.01); *G16H 30/40* (2018.01); *A61B 6/4441* (2013.01); *A61B 6/466* (2013.01); *A61B 2034/102* (2016.02); *A61B 2034/105* (2016.02); *G06T 2211/424* (2013.01); *G06T 2219/008* (2013.01); *G06T 2219/012* (2013.01)

(56) References Cited

U.S. PATENT DOCUMENTS

2013/0085774 A1* 4/2013 Chen ................. G09B 23/28
                                               705/2
2017/0035379 A1* 2/2017 Weingarten ............ G06T 7/62

FOREIGN PATENT DOCUMENTS

DE    102011083703 A1   4/2013
EP         3127485 A1   2/2017

* cited by examiner

METHOD OF IMAGE SUPPORT FOR A PERSON CARRYING OUT A MINIMALLY INVASIVE PROCEDURE WITH AN INSTRUMENT IN A PROCEDURE SITE OF A PATIENT, X-RAY APPARATUS, COMPUTER PROGRAM AND ELECTRONICALLY READABLE DATA CARRIER

CROSS-REFERENCE TO RELATED APPLICATION

This application claims the benefit, under 35 U.S.C. § 119, of German patent application DE 10 2017 203 438.6, filed Mar. 2, 2017; the prior application is herewith incorporated by reference in its entirety.

BACKGROUND OF THE INVENTION

Field of the Invention

The invention relates to a method of image support for a person carrying out a minimally invasive procedure with an instrument in a procedure site of a patient, wherein one two-dimensional X-ray image respectively of the procedure site is recorded by an X-ray apparatus in at least two recording geometries implementing different projection directions and chosen specific to the procedure, in particular by the person. In addition, the invention relates to an X-ray apparatus, to a computer program and to an electronically readable data carrier.

With minimally invasive surgical procedures, for example in traumatology, the appropriate medical instruments, for example tools and/or implants, have to be positioned in a minimally invasive manner and with a high degree of accuracy, for example on the bone. For this purpose it has been proposed that the correct placement/movement is monitored with the aid of an X-ray apparatus, for example a mobile X-ray apparatus having a C-arm. One problem here however is that the two-dimensional X-ray images are projection images, which do not provide any clear information about the three-dimensional structure of the depicted objects. It is therefore known that the person carrying out the procedure, in particular a doctor, records X-ray images from a plurality of projection directions in order to be able to assess all fundamental aspects. However, when adjusting the medical instruments and when approaching new recording geometries with the X-ray apparatus, for example a C-arm, undesirable movements can occur between the medical instrument and the anatomy in the procedure site. The consequence of this is that the person carrying out the procedure has to approach the various recording geometries, for example C-arm positions, several times in order to ensure the correct positioning of the medical instrument.

In practice the person carrying out the procedure therefore changes the recording geometry until they are sure of the positioning of the medical instrument. If three-dimensional reproductions of the procedure site are available, for example slices from magnetic resonance, computerized tomography or the like, it has also already been proposed that the medical instrument tracked by a position-determining system is displayed after successful spatial registering within a preoperative three-dimensional image data set of this kind. Position-determining systems of this kind, which are also known as tracking systems, can operate for example electromagnetically, by use of optical markers and the like, with it also having been proposed to use markers in the X-ray image. The medical instrument can therefore be displayed in the three-dimensional image data set from any viewing direction. One problem here, however, is that the anatomy in the procedure site displayed in this connection can differ to a greater or lesser extent as a result of the procedure from the actual, current anatomy in the procedure site.

SUMMARY OF THE INVENTION

The invention is therefore based on the object of disclosing an image support method, which is improved by contrast, for persons carrying out a minimally invasive procedure.

To achieve this object it is provided according to the invention in a method of the type mentioned in the introduction that a three-dimensional model data set of the procedure region is reconstructed by iterative reconstruction from the X-ray images, wherein at least one two-dimensional supporting image corresponding to one of the recording geometries is determined by incorporating at least one item of further information by reprojection of the model data set supplemented by the further information, and is displayed for the user.

Methods of iterative reconstruction (often also called: algebraic reconstruction) of three-dimensional data sets from two-dimensional projection images are already largely known in the prior art. With iterative reconstruction methods of this kind, a three-dimensional model—the three-dimensional model data set—is ultimately calculated, which explains the recorded X-ray images (projection images). Different virtual comparison images are stimulated during the iterative reconstruction from the three-dimensional model data set to be determined and these are compared with the recorded X-ray images. The three-dimensional model data set is then iteratively optimized by minimizing the errors between the simulated comparison images and the recorded X-ray images. An iterative reconstruction method of this kind can also be carried out with a small number of X-ray images, in other words with sparsely occupied coverage in respect of the projection directions, wherein there is then an underdetermining, however, and the resulting three-dimensional model data set only inadequately describes the anatomy for a large number of applications.

In respect of the present invention it has been recognized, however, that a three-dimensional model data set resulting from the X-ray images is underdetermined as a whole and is extremely inaccurate but has the optimum quality precisely for the recording geometries in which the X-ray images were recorded. In the application described here, these recording geometries conventionally chosen by the person carrying out the procedure to be specific to the procedure are the relevant projection directions, however, in which the person would like to have information reproduced, for example the position of objects relative to the anatomy. If, in addition, it is considered that three-dimensional model objects, such as, for example, an instrument model of the tracked medical instrument used, can be positioned in a three-dimensional model data set of this kind, an almost perfect simulated X-ray image, in other words, the at least one supporting image, can be determined for a three-dimensional model of the procedure site supplemented in this way by addition of a further item of information, and the recording geometries, in other words, projection directions, for which a recorded X-ray image was considered during iterative reconstruction. It should also be noted that the recording geometries do not necessarily have to be chosen by the person carrying out the procedure. Instead, it is also conceivable for them to be at least partially automatically determined, for example by evaluating a three-dimensional preoperative image data set.

The person carrying out the procedure, for example a treating doctor, is therefore given the option of simulating X-ray images, which have already been recorded, again in order to have model objects, for example the medical instrument or added geometric scan objects, displayed in a three-dimensional context, for example in respect of the masking. What is essential here is that during reprojection (often also called forward projection or simulation of an X-ray image), precisely those recording geometries are used for which the three-dimensional model is optimized.

It can be provided that less than 10, in particular less than 5, recording geometries chosen specific to the procedure are used. In practice it has been found that during a minimally invasive procedure by the person carrying it out, usually only about 2 to 4 different recording geometries, in other words, projection directions, are chosen to reproduce the desired information. Although the three-dimensional model reconstructed herefrom or, specifically, the three-dimensional model data set is inaccurate for other projection directions, it is still optimized precisely for these chosen projection directions specific to the procedure and delivers outstanding results without a renewed approaching of the recording geometry with subsequent recording of a current X-ray image being necessary.

To summarize, the invention therefore proposes associating the two-dimensional X-ray images recorded during a procedure in order to determine an inaccurate or incomplete three-dimensional model data set of the underlying anatomy in the procedure site, in which, in contrast to a sufficiently accurate, complete three-dimensional model data set, the expected image quality is sufficient only for simulated projection images, whose recording geometry corresponds to that of an acquired X-ray image considered in the iterative reconstruction. Supporting images can therefore be generated for the person without X-ray images having to be specially recorded. This enables a significant reduction in the time of the minimally invasive procedure as well as in the radiation dose administered, in particular if the position of a model object, in particular the medical instrument, actually acquired using X-rays can be acquired otherwise.

Use of the three-dimensional model data set has further advantages compared to an intended solution in which simply only the model object added by the further information is forward projected and superimposed in the X-ray images. Firstly, due to the fact that the iterative reconstruction is performed on the basis of a plurality of X-ray images, a smaller shift in the anatomy, which occurs, for example, due to inaccuracies in the determination of the recording geometries or small movements of the patient, between recording of these X-ray images is automatically compensated, resulting in a consistent overall image. Secondly, however, anatomical objects are, at least in principle, depicted in the three-dimensional model data set, so the arrangement relative to these anatomical objects is also given with the addition of an item of further information in the three-dimensional model data set, therefore masking effects can be correctly reproduced.

In a first advantageous, specific application of the present invention it can be provided that as a further item of information, a three-dimensional instrument model on the basis of a current item of position information of the instrument in the procedure site is inserted into the model data set and the projection of the instrument model into supporting images showing the recording geometries are determined and displayed. If, therefore, a three-dimensional item of position information of the instrument, which can of course also include an item of orientation information in addition to purely an item of location information, can be determined, a corresponding instrument model can be included as further information in the three-dimensional model data set with the current position and orientation. Instrument models of this kind can be easily derived, for example by means of dimensions and material properties of the medical instrument known from databases, which instrument can be, for example, a tool and/or an implant. Without recording X-ray images, or at least with a reduced number of X-ray images, the person is therefore provided with supporting images, which show the instrument at its current position relative to the anatomy in the procedure site. This enables highly accurate, time-efficient and reliable monitoring of the instrument positioning.

The item of position information can preferably be determined by a position-determining system registered with the X-ray apparatus and/or from a two-dimensional localizing image of the X-ray apparatus. A first possibility for determining the three-dimensional item of position information is therefore the use of a position-determining system. A position-determining system of this kind can be configured for example as an electromagnetic position-determining system or optical position-determining system. Position-determining systems of this kind have already been described in the prior art, just like possibilities for registering image data or coordinate systems of imaging devices having such position-determining systems. Within the context of the present invention it can, however, also be expedient if a two-dimensional localizing image of the X-ray apparatus is used to determine the item of position information. It is for example conceivable to determine the three-dimensional position by special X-ray markers, which can be arranged in particular on the instrument. For example, conclusions can be drawn here from the display size. An advantageous embodiment also provides that a three-dimensional item of position information is determined from the shaping of the instrument and the corresponding display in the localizing image. To summarize, it can therefore be provided that when using a single localizing image, the three-dimensional item of position information is determined on the basis of at least one marker and/or the shaping of the instrument. If the X-ray apparatus itself is used to determine the three-dimensional item of position information of the instrument, additional equipment and additional expenditure, for example for registering, are advantageously omitted.

It should also be noted at this point that if one of the recording geometries specific to the procedure is used, the localizing image can of course also be used as an X-ray image or an updated X-ray image, in particular also to update the three-dimensional model data set, which will be discussed in more detail below.

In the context of an instrument model, as further information it is also expedient if in the case of an instrument located in the procedure site, as early as during recording of at least some of the X-ray images, this instrument is segmented in the X-ray images and/or in the model data set and removed. If the X-ray images, from which the three-dimensional model data set is calculated, are therefore recorded with the instrument already located in the procedure site, the instrument also appears in the three-dimensional model data set, if the instrument is visible as a result of X-ray radiation, and this is undesirable since it can irritate the user to see a plurality of instruments. Methods of image processing are therefore expediently used to detect, segment and remove the instrument in the X-ray images or also in the model data set.

For example, a workflow is conceivable in which the person first of all acquires the X-ray images from the different projection directions in order to then change the position of the tracked instrument. By means of the inventive method, the new position of the instrument can then be updated and displayed on the supporting images, in other words, simulated X-ray images, for the projection directions previously approached.

A further advantageous field of application of the present invention is the performance of scans or other plans in the procedure site, because there is often a desire to determine for example the distance between particular anatomical structures, their diameter, area thereof and the like, for example, to be able to choose a suitable medical instrument, for example a screw as an implant.

To that effect an advantageous embodiment of the present invention provides that for determining at least one of the at least one item of further information about at least two selection points chosen as the selection image by the user in one of the X-ray images or a supporting image, one three-dimensional position respectively of the selection point is determined in the model data set by searching along a beam, defined in the recording geometry of the selection image, in which the selection points were chosen, which beam crosses the selection point, for a jump in intensity in at least one search direction in the model data set, the position of which is chosen as the three-dimensional position of the selection point, and at least one supporting image re-projected with the selection points as further information in a different recording geometry to that of the selection image, in which the selection points were chosen, is determined.

In other words, the user, in particular therefore the person, can choose selection points in a selection image, which can be one of the X-ray images, but also a supporting image, which points can define for example a distance or an area. The presence of the three-dimensional model data set accordingly makes it possible to at least assume which three-dimensional position of the selection point the user could have intended, because the recording geometry describes the course of the beam, which ends at the selection point, so a search can be conducted along this beam for jumps in intensity, which indicate distinguished three-dimensional points which could have been intended as a three-dimensional selection point. Such a search process can also be called "picking" and is carried out for each of the selection points. The result are three-dimensional positions for the selection points, which are used to be able to display the assumed selection points even in supporting images of at least one other recording geometry, so the person can check whether the correct selection point in three dimensions was actually found.

In an embodiment that is easy to implement, it can be provided that the search direction is chosen perpendicular to the beam direction. As has already been illustrated, once the three-dimensional model data set is at its most accurate in respect of the recording geometries, in which X-ray images also exist, as an alternative or in addition it has proven to be expedient to use as search directions beam directions of the recording geometry of at least the supporting image or selection image, preferably of all recording geometries, through a point of the beam currently being examined. Analysis in the three-dimensional model data set is therefore performed where the most reliable information exists.

In a particularly advantageous embodiment of the invention it can be provided that the three-dimensional position of the selection point is adjusted as a function of a user-side shift of the selection point in the supporting image along the associated beam projected in the supporting image. If a selection point is defined in a selection image, the potential three-dimensional layers are depicted, if no other information exists, as a line in a supporting image of the recording geometry of the other direction of projection. If determination of the three-dimensional position of the selection point by searching for jumps in intensity along the beam according to the selection image is accordingly understood as a first assumption, the user has the choice of still changing this three-dimensional position by shifting the selection point illustrated in the supporting image. The shift is then limited to the line in the supporting image. If a plurality of jumps in intensity was found along the beam and, for example, the first and/or largest one assumed to mark the three-dimensional position of the selection point, the positions of the other jumps in intensity can also be purposefully provided in the case of shifts. The person can therefore not only check whether the three-dimensional position of the selection point was correctly chosen automatically, but, if this is not the case, suitably adapt it in a manner that is ideally supported.

Preferably at least one dimension of a geometric shape spanned by the selection points can be determined and output on the basis of the three-dimensional positions of the selection points, in particular in the case of two selection points, a distance between the selection points. Ultimately this provides a workflow overall, which allows a measurement of distances in the three-dimensional space (instead of only in the two-dimensional space of an X-ray image). The user is purposefully supported in the correct definition of three-dimensional points in that the background knowledge of the model data set is used at least in respect of the projection directions of the recording geometries specific to the procedure.

A workflow resulting from this could, for example, contain that after recording the X-ray images in the different projection directions, the person defines, for example by means of a mouse, two selection points on an X-ray image, which in turn define a line on the X-ray image. An arithmetic device that carries out the invention, for example an image system of an X-ray apparatus, calculates the most probable three-dimensional positions for both selection points, in particular as described of intensity transitions in the three-dimensional model data set along the beam path, after which the line (including the selection points) defined by the discovered 3D coordinates of the selection points is displayed on supporting images, in other words simulated X-ray images, of the other recording geometries previously approached. Using the supporting image, the person checks the correct positioning and corrects it if required. The length of the line can then be calculated as the distance of the selection points by the arithmetic device carrying out the method, in particular the image system of the X-ray apparatus, and can be communicated to the person.

One development of the invention also provides that the model data set is updated when a current X-ray image is rerecorded in at least one of the recording geometries, in particular after 2D-3D registering of the model data set and the current X-ray image. In this way, inaccuracies due to sensors, patient movements and the like can be minimized in that 2D-3D registering takes place before new, current X-ray images are considered in the model data set.

It should be noted at this point that in order to carry out the method, the X-ray apparatus, or correspondingly moveable components, must obviously be capable of automatically determining their settings and therefore the recording geometries, although this is possible in a great deal of modern X-ray equipment anyway.

In addition to the method, the present invention also relates to X-ray apparatus, having a controller configured for carrying out the inventive method. All statements in respect of the inventive method can be transferred analogously to the inventive X-ray apparatus, with which the advantages can likewise be obtained therefore. In particular, the X-ray apparatus can have a C-arm on which an X-ray emitter and an X-ray detector are arranged opposite each other. Furthermore, it can be provided that the controller is implemented as part of an image system. In addition to a recording control unit for controlling the recording operation of the X-ray apparatus, the controller can comprise a reconstruction unit for determining the three-dimensional model data set and a reprojection unit for determining supporting images.

An inventive computer program can, for example, be loaded directly into a storage device of a controller of an X-ray apparatus and has program means to carry out the steps of a method described herein when the computer program is run in the controller of the X-ray apparatus. The computer program can be saved on an inventive electronically readable data carrier, which consequently contains electronically readable control information stored thereon, which comprises at least the computer program and is configured in such a way that it carries out a method described herein when the data carrier is used in a controller of an X-ray apparatus. The data carrier can be a non-transient data carrier, for example a CD-ROM.

Other features which are considered as characteristic for the invention are set forth in the appended claims.

Although the invention is illustrated and described herein as embodied in a method of image support for a person carrying out a minimally invasive procedure with an instrument in a procedure site of a patient, an X-ray apparatus, a computer program and an electronically readable data carrier, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
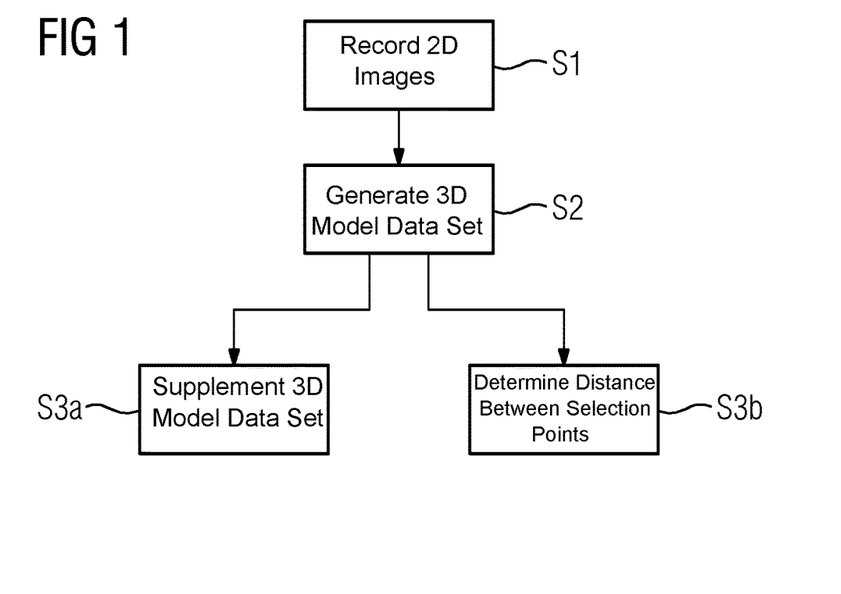
FIG. 1 is a flowchart of an exemplary embodiment of a method according to the invention.

Referring now to the figures of the drawings in detail and first, particularly to FIG. 1 thereof, there is shown a basic flowchart of an exemplary embodiment of an inventive method. A person carrying out a minimally invasive procedure is to be supported by images. To enable this, it is firstly provided in a step S1 that by means of an X-ray apparatus, two-dimensional X-ray images are recorded using an X-ray apparatus in recording geometries chosen by the person and which correspond to different projection directions specific to the procedure. In the present case this is an X-ray apparatus having a C-arm, which can also be flexibly positioned at the procedure site in order to record the X-ray images. If an example from traumatology is used, the person can, for example, select the recording geometries specific to the procedure such that the correct position of an implant as the medical instrument can be optimally assessed. In the present case, by way of example two X-ray images, therefore two recording geometries specific to the procedure, are considered, with, for example, three or four X-ray images from different projection directions also being conceivable. In the present case, the X-ray images are recorded without the medical instrument; in other cases it is provided that the medical instrument is eliminated afterwards.

By iterative reconstruction a three-dimensional model data set of the procedure site of the patient depicted in the X-ray images is generated in a step S2 from the two-dimensional X-ray images. It is accepted here that the model data set is underdetermined and cannot completely correctly reproduce the three-dimensional anatomy in the procedure site since it is sufficient in the present case to obtain correct images again with a reprojection in the recording geometries, and this is the case since optimally accurate reproduction of the X-ray images is the objective. This is shown schematically in FIG. 2. Shown by way of example are real anatomical structures 1 in the procedure site, with the two recording geometries considered here being indicated by the position of the X-ray emitter 2 and the respective acquisition regions 3. Also shown schematically are the respectively resulting X-ray images 4, showing projected images of the anatomical structures 1.

Figure 2:
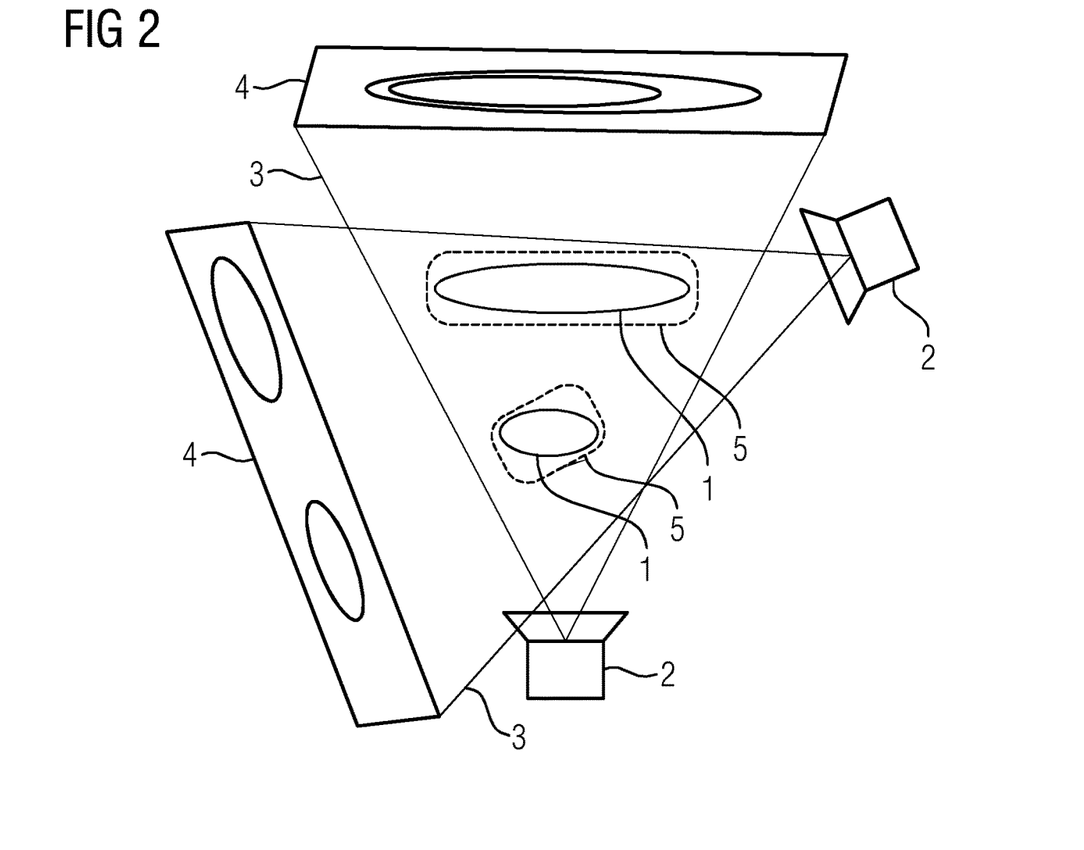
FIG. 2 is a schematic diagram relating to recording with different recording geometries and relating to determining the three-dimensional model data set.

If a three-dimensional model data set is generated by iterative reconstruction, then this does not reproduce the real anatomical structures 1 completely correctly, but as underdetermined, reconstructed anatomy objects 5, indicated here only highly schematically, which are characterized such that with reprojection from the three-dimensional model data set, the anatomical structures 1 are correctly displayed in reprojected simulated X-ray images. Potential smaller deviations/shifts were automatically determined by the iterative reconstruction process, so a consistent overall image was produced.

The three-dimensional model data set of step S2 produced in this way can now be used in various applications, which are identified in the present case by steps S3*a* and S3*b* in FIG. 1. Each of these applications involves the addition of further information, in particular an additional object, in the three-dimensional model data set and a reprojection in order to obtain a supporting image.

Figure 3:
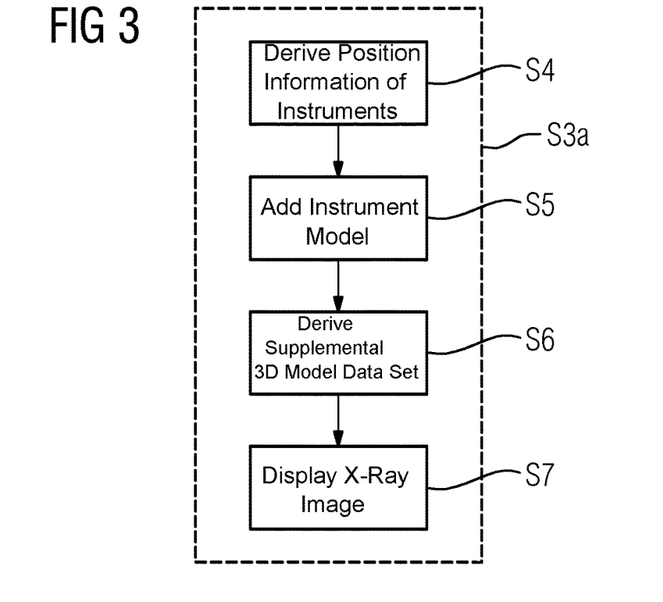
FIG. 3 is a flowchart relating to a first application of the inventive method.

FIG. 3 illustrates a first application by showing corresponding sub-steps of step S3*a* in more detail. This is intended to show the current position of a medical instrument used, in particular a tool and/or an implant, where re-recording of X-ray images in supporting images of the recording geometries specific to the procedure, therefore predetermined, has been at least partially avoided.

For this, first a three-dimensional item of position information of the medical instrument is determined in step S4. This includes a location as well as an orientation. For example, an electromagnetic and/or optical position-determining system can be used for determining the current three-dimensional item of position information. However, it is also conceivable to determine the current item of position information from a localizing image, in particular a single image, using the X-ray apparatus, with markers or preferably the geometric shaping of the medical instrument being used to also derive a three-dimensional item of localizing information from the single two-dimensional localizing image. If the two-dimensional localizing image was recorded in one of the recording geometries, it therefore forms a current X-ray image, and if it is to be used for updating the three-dimensional model data set, firstly 2D-3D registering with the three-dimensional model data set is carried out. The use of a position-determining system has the advantage that there is no further radiation exposure for the patient; the use of a localizing image of the X-ray apparatus has the advantage that no further equipment needs to be present and that any further equipment, specifically a position-determining system, does not even have to first be registered with the coordinate system of the X-ray apparatus, in particular the C-arm.

Owing to registering established, for example, during a calibration step when using a position-determining system or where a reference exists anyway when recording a localizing image, it is now possible to add, in a step S5, an instrument model to the three-dimensional model data set as further information, which model results primarily from geometric dimensions and attenuation properties of the instrument retrieved from a database.

Figure 4:
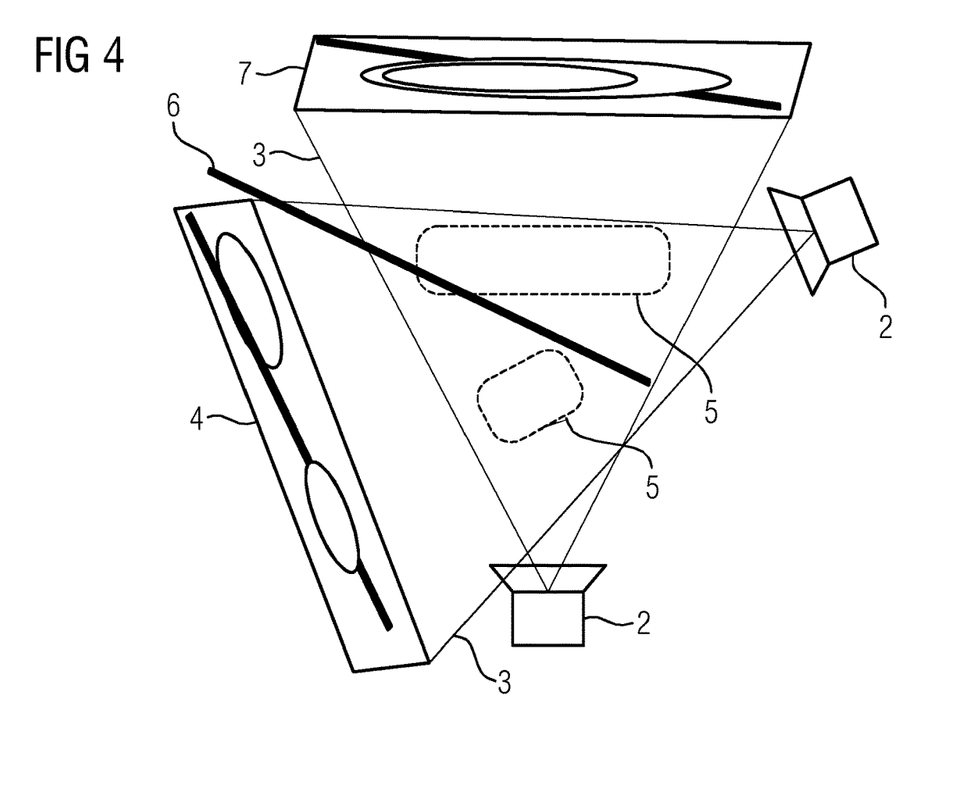
FIG. 4 is a schematic diagram relating to the generation of supporting images.

In a step S6 it is then possible to obtain by reprojection of the supplemented three-dimensional model data set, supporting images as simulated X-ray images in the recording geometries, and these can be displayed in a step S7. This process is illustrated again in more detail by the schematic diagram of FIG. 4. The indicated recording geometries specific to the procedure (position of X-ray emitter 2, acquisition regions 3) and the reconstructed anatomy objects 5 can again be seen. An instrument model 6 has been added. If a forward projection now takes place according to the recording geometries, supporting images 7 are obtained, which include an image of the medical instrument as well as the anatomy in the procedure site.

Figure 5:
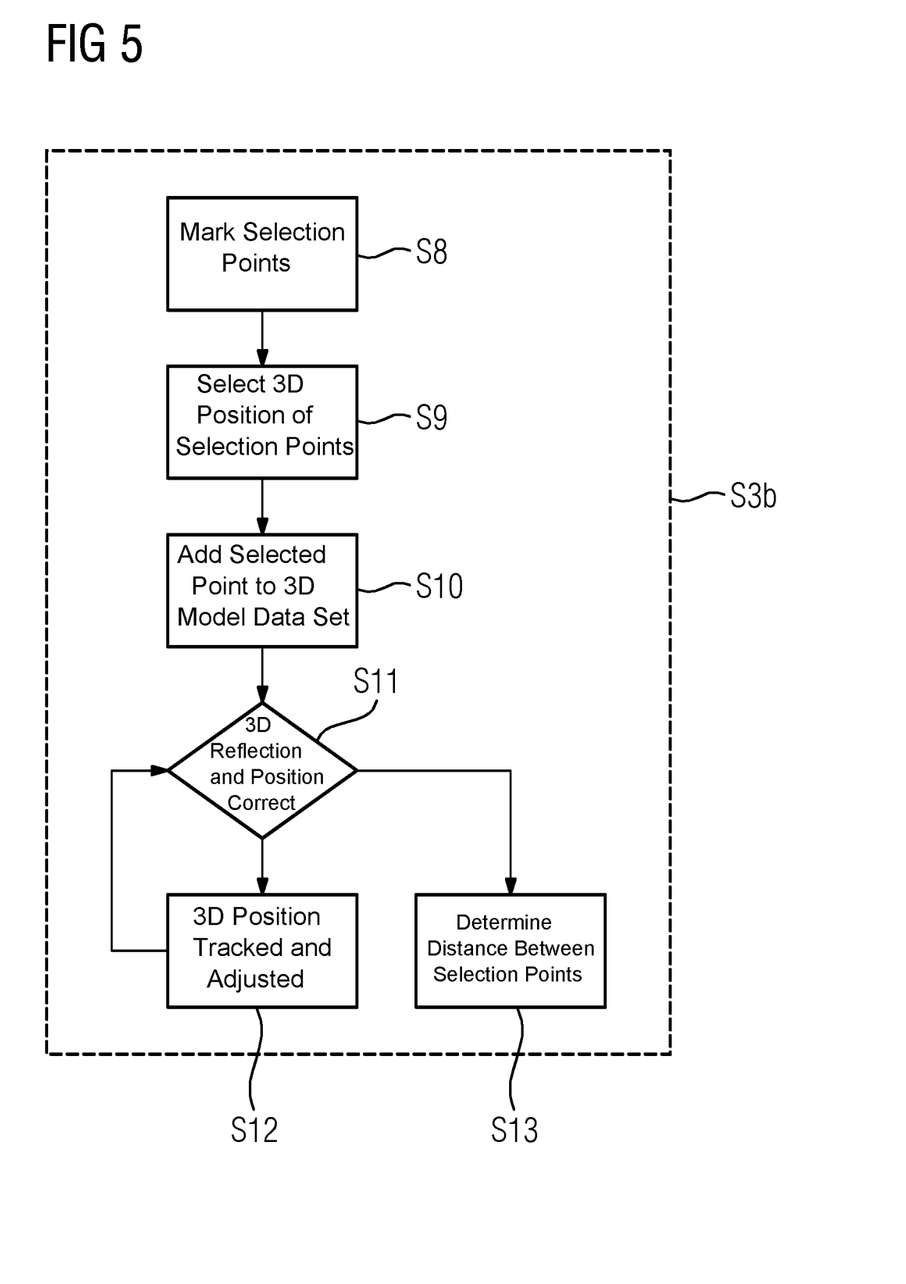
FIG. 5 is a flowchart relating to a second application of the inventive method.

FIG. 5 shows a further application by illustrating substeps of step S3b. There it is provided that a distance between two points in the procedure site is measured. In step S8 the person therefore first marks two selection points at appropriate (projected) positions in one of the X-ray images 4 or even a supporting image 7 (for simplification collectively called a selection image). In step S9 it should then be estimated within the context of a "picking" process which three-dimensional position of the selection points was intended, and this occurs with the aid of the three-dimensional model data set. This shall be illustrated in more detail with the aid of FIG. 6, which shows a selection point 9 marked by the user in the selection image 8. In the recording geometry of the selection image 8 this selection point 9 includes a beam 10, issuing from the X-ray emitter 2, on which beam the selection point must lie. It is therefore provided in step S9 that a search is made along this beam 10 for jumps in intensity in at least one search direction 11, with one jump being given at the three-dimensional position 12 by the indicated edge of the reconstructed anatomy object 5. The search direction 11 can be chosen as the beam direction in the other recording geometry at the respective three-dimensional position 12 along the beam 10 or be chosen perpendicular to the beam 10. With a plurality of further recording geometries, preferably all of their beam directions are used as search directions.

Figure 6:
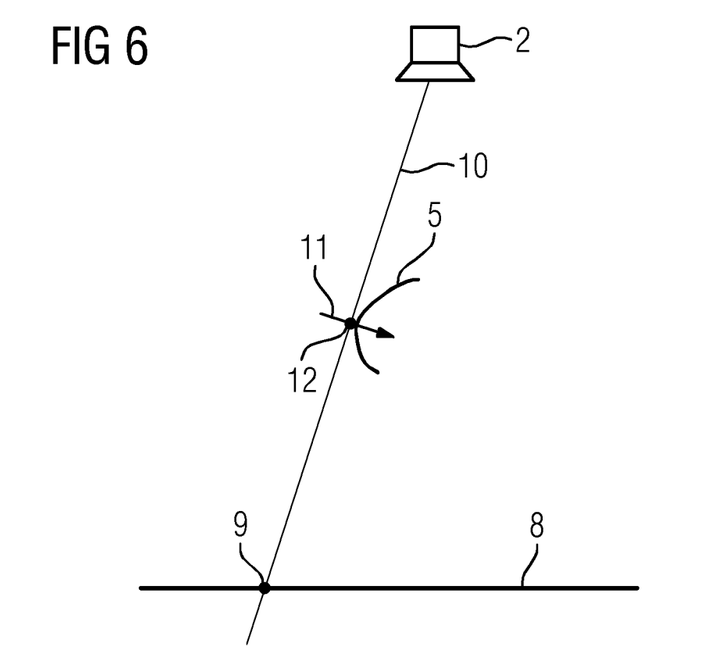
FIG. 6 is a schematic diagram relating to finding a three-dimensional position of a selection point.

The first found or most significant jump in intensity marks the three-dimensional position 12 of the selection point 9, as is automatically estimated. The selection point is then added to the three-dimensional model data set at this three-dimensional position 12 as further information and a reprojection takes place in step S10, in other words a forward projection, from the three-dimensional model data set supplemented in this way in the other recording geometry in order to obtain a supporting image in which a position of the respective selection points 9 can likewise be seen.

In a step S11 the person can then check whether the assumption of the three-dimensional position 12, as is reflected in the supporting image, is correct. If this is not the case, they can shift the respective selection point 9 in the supporting image along the projection of the beam 10 to the position actually desired by way of corresponding operating means, for example a mouse. The three-dimensional position 12 of the selection point 9 is accordingly tracked and adjusted. Once this has occurred in step S12, the person can check again in step S11 whether the correct three-dimensional position of the selection points 9 is given.

Once the three-dimensional position 12 of the selection points 9 has been confirmed, the arithmetic device, in particular an image system of a controller of the X-ray apparatus, carrying out the method automatically determines in a step S13 the distance between the selection points, which was sought, and displays it for the person.

Figure 7:
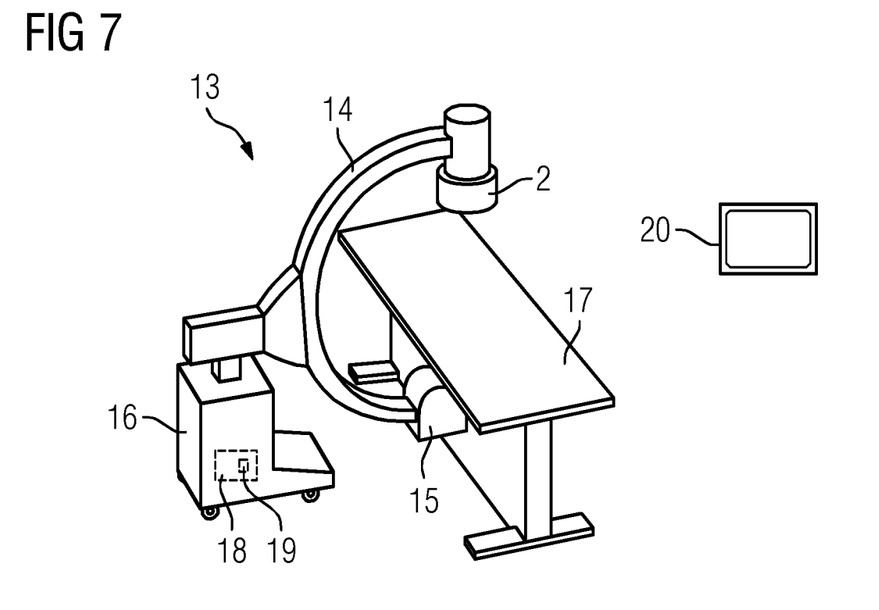
FIG. 7 is a diagrammatic, perspective view an inventive X-ray apparatus.

FIG. 7, finally, shows a schematic diagram of an inventive X-ray apparatus 13, which contains an at least pivotal C-arm 14 on which the X-ray emitter 2 and an X-ray detector 15 are arranged opposite each other. The C-arm 14 is arranged on a mobile unit 16 in order to be able to move the X-ray apparatus 13 in the procedure room and for example, if necessary, move it up to an appropriate examination table 17. A controller 18, which controls operation of the X-ray apparatus 13, is only indicated. Current positions of the C-arm 14 or of the X-ray detector 15/X-ray emitter 2, and therefore currently adjusted recording geometries, can be automatically determined by the controller 18. In the present case it is also configured for carrying out the inventive method, wherein the image system 19 with which calculations on iterative reconstruction and reprojection can be performed particularly easily is also used, for example by means of an appropriate reconstruction unit and an appropriate reprojection unit. Also arranged in the procedure room is a display device 20 in order to be able to display the supporting images 7 and the X-ray images 4 accordingly.

Although the invention has been illustrated and described in detail by the preferred exemplary embodiment, it is not limited by the disclosed examples and a person skilled in the art can derive other variations herefrom without departing from the scope of the invention.

The following is a summary list of reference numerals and the corresponding structure used in the above description of the invention:

1 structure
2 X-ray emitter
3 acquisition region

4 X-ray image
5 anatomy object
6 instrument model
7 supporting image
8 selection image
9 selection point
10 beam
11 search direction
12 position
13 X-ray apparatus
14 C-arm
15 X-ray detector
16 mobile unit
17 examination table
18 controller
19 image system
20 display device

The invention claimed is:

1. A method of image support for a person carrying out a minimally invasive procedure with an instrument in a procedure site of a patient, which comprises the steps of:
recording one two-dimensional X-ray image respectively of the procedure site by an X-ray apparatus in at least two recording geometries implementing different projection directions and chosen specific to the minimally invasive procedure;
reconstructing a three-dimensional model data set of the procedure site by iterative reconstruction from two-dimensional X-ray images;
inserting a three-dimensional instrument model into the three-dimensional model data set on a basis of a current item of position information of the instrument in the procedure site;
determining at least one two-dimensional supporting image corresponding to one of the recording geometries and incorporating the instrument model by reprojection of the three-dimensional model data set supplemented by the three-dimensional instrument model; and
displaying the three-dimensional model data set and the at least one two-dimensional supporting image to a user.

2. The method according to claim 1, which further comprises using less than 10 of the recording geometries chosen specific to the minimally invasive procedure.

3. The method according to claim 1, which further comprises determining the current item of position information by a position-determining system registered with the X-ray apparatus and/or from a two-dimensional localizing image of the X-ray apparatus.

4. The method according to claim 3, wherein when using a single localizing image, a three-dimensional item of position information is determined on a basis of at least one marker and/or a shaping of the instrument.

5. The method according to claim 1, wherein in a case of the instrument being disposed in the procedure site as early as during recording of at least some of the two-dimensional X-ray images, it is segmented and removed in the two-dimensional X-ray images and/or the three-dimensional model data set.

6. A method of image support for a person carrying out a minimally invasive procedure with an instrument in a procedure site of a patient, which comprises the steps of:
recording one two-dimensional X-ray image respectively of the procedure site by an X-ray apparatus in at least two recording geometries implementing different projection directions and chosen specific to the minimally invasive procedure;
reconstructing a three-dimensional model data set of the procedure site by iterative reconstruction from two-dimensional X-ray images, wherein at least one two-dimensional supporting image corresponding to one of the recording geometries is determined by incorporating at least one item of further information by reprojection of the three-dimensional model data set supplemented by the further information; and
displaying the three-dimensional model data set to a user;
for determining at least one of the at least one item of further information about at least two selection points chosen by the user as a selection image in one of the two-dimensional X-ray images or the two-dimensional supporting image, one three-dimensional position respectively of a selection point is determined in the three-dimensional model data set by searching along a beam, defined in a recording geometry of the selection image, in which the selection points were chosen, where the beam crosses the selection point, for a jump in intensity in at least one search direction in the three-dimensional model data set, the position of which is chosen as the three-dimensional position of the selection point; and
at least one supporting image, reprojected with the selection points as further information in a different recording geometry to that of the selection image, in which the selection points were chosen, is determined.

7. The method according to claim 6, wherein that directions and/or beam directions, perpendicular to the beam, of a recording geometry of at least the supporting image or the selection image, through a point of the beam currently being examined, are used as search directions.

8. The method according to claim 6, which further comprises adjusting the three-dimensional position of the selection point in dependence on a user-side shift of a projected selection point in the supporting image along the beam projected into the supporting image.

9. The method according to claim 6, which further comprises determining and outputting at least one measure of a geometric form spanned by the selection points on a basis of three-dimensional positions of the selection points.

10. The method according to claim 1, wherein when a current X-ray image is rerecorded, the three-dimensional model data set is updated in at least one of the recording geometries.

11. The method according to claim 1, which further comprises using less than 5 of the recording geometries chosen specific to the minimally evasive procedure.

12. The method according to claim 6, wherein that directions and/or beam directions, perpendicular to the beam, of all the recording geometries of at least the supporting image or the selection image, through a point of the beam currently being examined, are used as search directions.

13. The method according to claim 6, which further comprises determining and outputting at least a distance spanned between two of the selection points on a basis of three-dimensional positions of the two selection points.

14. The method according to claim 1, wherein when a current X-ray image is rerecorded, the model data set is updated in at least one of the recording geometries after 2D-3D registering of the three-dimensional model data set and the current X-ray image.

15. An X-ray apparatus, comprising:
a controller programmed to perform a method of image support for a person carrying out a minimally invasive procedure with an instrument in a procedure site of a patient, which comprises the steps of:

recording one two-dimensional X-ray image respectively of the procedure site by an X-ray apparatus in at least two recording geometries implementing different projection directions and chosen specific to the minimally invasive procedure;

reconstructing a three-dimensional model data set of the procedure site by iterative reconstruction from two-dimensional X-ray images;

inserting a three-dimensional instrument model into the three-dimensional model data set on a basis of a current item of position information of the instrument in the procedure site;

determining at least one two-dimensional supporting image corresponding to one of the recording geometries and incorporating the instrument model by reprojection of the three-dimensional model data set supplemented by the three-dimensional instrument model; and displaying the three-dimensional model data set and the at least one two-dimensional supporting image to a user.

16. A non-transitory, electronically readable data carrier having computer executable instruction for performing a method of image support for a person carrying out a minimally invasive procedure with an instrument in a procedure site of a patient according to claim 1.

* * * * *